US011247002B2

(12) United States Patent
McLoughlin et al.

(10) Patent No.: US 11,247,002 B2
(45) Date of Patent: Feb. 15, 2022

(54) CONTROL DEVICE FOR A MEDICAL AEROSOL DELIVERY DEVICE

(71) Applicant: KONINKLIJKE PHILIPS N.V., Eindhoven (NL)

(72) Inventors: Neal McLoughlin, Bognor Regis (GB); Ivan Prince, Chichester (GB); Ian Philip Rabbetts, Hayling Island (GB)

(73) Assignee: Koninklijke Philips N.V., Eindhoven (NL)

( * ) Notice: Subject to any disclaimer, the term of this patent is extended or adjusted under 35 U.S.C. 154(b) by 704 days.

(21) Appl. No.: 15/736,846

(22) PCT Filed: Jun. 22, 2016

(86) PCT No.: PCT/EP2016/064330
§ 371 (c)(1),
(2) Date: Dec. 15, 2017

(87) PCT Pub. No.: WO2017/001251
PCT Pub. Date: Jan. 5, 2017

(65) Prior Publication Data
US 2018/0177959 A1 Jun. 28, 2018

(30) Foreign Application Priority Data
Jun. 29, 2015 (EP) .................................. 15174219

(51) Int. Cl.
*A61M 15/00* (2006.01)
*A61B 5/087* (2006.01)
(Continued)

(52) U.S. Cl.
CPC .......... *A61M 15/0066* (2014.02); *A61B 5/087* (2013.01); *A61B 5/4839* (2013.01);
(Continued)

(58) Field of Classification Search
CPC .......... A61M 15/0065; A61M 15/0066; A61M 2016/0015; A61M 2230/42;
(Continued)

(56) References Cited

U.S. PATENT DOCUMENTS

| 5,509,404 A | 4/1996 | Lloyd |
| 5,542,410 A | 8/1996 | Goodman |
| 5,890,490 A * | 4/1999 | Aylsworth .......... A61M 16/024 128/203.12 |
| 6,584,971 B1 | 7/2003 | Denyer |

(Continued)

*Primary Examiner* — Victoria Murphy
(74) *Attorney, Agent, or Firm* — Daniel H. Brean

(57) ABSTRACT

The invention relates to a control device (10) for a medical aerosol delivery device (2), a medical aerosol delivery system, a method for controlling a medical aerosol delivery device (2), a computer program element for controlling such device or system, and a computer readable medium having stored such computer program element. The control device is configured to provide inhalation length data and to select an aerosol delivery mode from at least a first aerosol delivery mode or a different, second aerosol delivery mode based on the provided inhalation length data. The first aerosol delivery mode and the different, second aerosol delivery mode are one of a target inhalation mode, a tidal breathing mode, a continuous aerosol delivery mode and breath-actuated delivery mode. Optionally, the control device (10) comprises a provision unit (11) and a control unit (13). The provision unit (11) is configured to provide inhalation length data. The processing unit may be configured to select either a first aerosol delivery mode or a different, second aerosol delivery mode based on the provided inhalation length data. The medical aerosol delivery system comprises an aerosol delivery device (2) and such control device (10). The control device (10) is configured to control the aerosol delivery device (2). The aerosol delivery device (2) is configured to deliver aerosol to a user.

18 Claims, 2 Drawing Sheets

Figure 1:
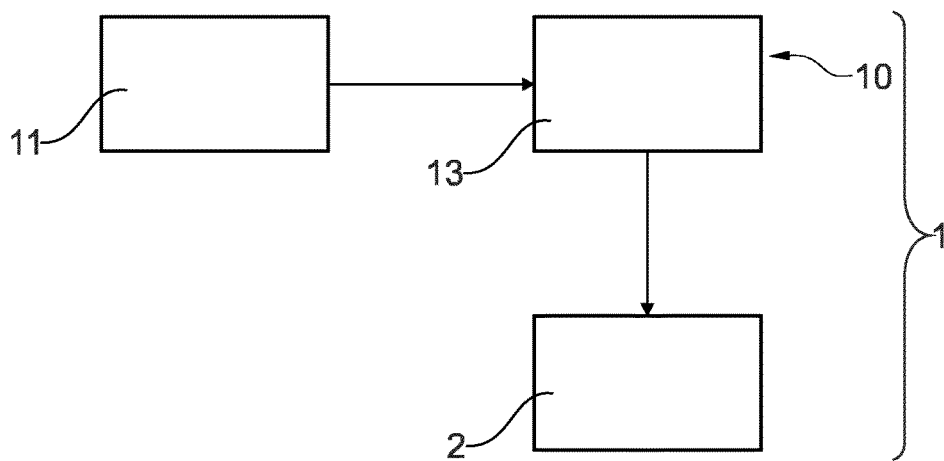

(51) Int. Cl.
*A61M 11/00* (2006.01)
*A61B 5/00* (2006.01)
*A61M 16/00* (2006.01)

(52) U.S. Cl.
CPC ...... *A61M 11/005* (2013.01); *A61M 15/0065* (2013.01); *A61M 2016/0015* (2013.01); *A61M 2205/52* (2013.01); *A61M 2205/581* (2013.01); *A61M 2205/582* (2013.01); *A61M 2205/583* (2013.01); *A61M 2230/42* (2013.01)

(58) Field of Classification Search
CPC .. A61M 2205/52; A61B 5/087; A61B 5/4836; A61B 5/4839
USPC .................................................. 128/203.14
See application file for complete search history.

(56) References Cited

U.S. PATENT DOCUMENTS

| | | |
|---|---|---|
| 8,464,706 B2 | 6/2013 | Crockford |
| 8,820,316 B2 | 9/2014 | Crockford |
| 2003/0136400 A1 | 7/2003 | Klimowicz |
| 2005/0087189 A1 | 4/2005 | Crockford |
| 2006/0243277 A1* | 11/2006 | Denyer ............. A61M 15/0085 128/202.22 |
| 2007/0125370 A1 | 6/2007 | Denyer |
| 2009/0025714 A1* | 1/2009 | Denyer ................. A61M 15/00 128/200.23 |
| 2009/0025718 A1 | 1/2009 | Denyer |
| 2011/0282173 A1* | 11/2011 | Fonduca ............ A61B 5/14532 600/365 |
| 2015/0099994 A1 | 4/2015 | Spencer |
| 2015/0283339 A1* | 10/2015 | Mahadevan .......... A61M 15/00 128/203.14 |

* cited by examiner

CONTROL DEVICE FOR A MEDICAL AEROSOL DELIVERY DEVICE

CROSS-REFERENCE TO RELATED APPLICATIONS

This patent application claims the priority benefit under 35 U.S.C. § 371 of international patent application no. PCT/EP2016/064330, filed Jun. 22, 2016, which claims the benefit of European Patent Application No. 15174219.4, filed on Jun. 29, 2015, the contents of which are herein incorporated by reference.

FIELD OF THE INVENTION

The invention relates to a control device for a medical aerosol delivery device, a medical aerosol delivery system, a method for controlling a medical aerosol delivery device, a computer program element for controlling such device or system, and a computer readable medium having stored such computer program element.

BACKGROUND OF THE INVENTION

US 2009/025718 A1 discloses an aerosol drug delivery apparatus. The apparatus may include a reservoir constructed to contain a predetermined dose of a liquid drug, an aerosol generator in communication with the reservoir, and a power source arranged to deliver power to the aerosol generator in order to produce an aerosolized form of the dose that can be administered to a patient. The apparatus may maintain consistent aerosol drug delivery treatments, for example, by way of a breath measuring mechanism that monitors the patient's breathing pattern during the administration of the dose and a controller configured to vary the power level at which the power source during the administration of the dose based on the monitored breathing pattern.

EP 1 525 893 A2 discloses a drug delivery apparatus in form of a nebulizer. The nebulizer comprises means for determining a duration of a pulse of atomisation during inspiration, such means including means for measuring the patient's tidal volume, timing means for measuring the duration of inspiration, means for storing an estimate of the volume of the patient's upper airway and means for calculating the duration of the pulse on the basis of the measurements and stored estimate. An alternative nebuliser comprises means for predicting the tidal volume including means for measuring the patient's peak flow, timing means for measuring duration of inspiration and means for calculating the tidal volume on the basis of the measurements; and means for atomising a medication, means for monitoring the patient's breathing pattern and means for controlling the atomising means to provide pulses of varying length and proportion of the inspiratory phase in dependence on the breathing pattern.

Figure 5:
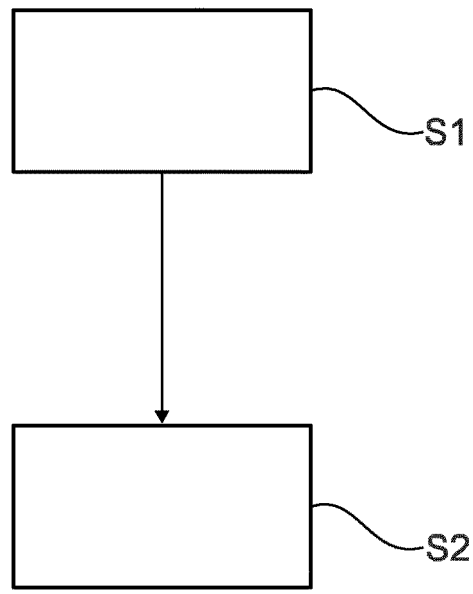

Such conventional nebulizers or medical aerosol delivery devices comprise a control unit to implement an adaptive aerosol delivery algorithm to control a timing of aerosol drug delivery into a user's or patient's breathing pattern. The adaptive aerosol delivery algorithm comprises two modes called TIM (target inhalation mode) and TBM (tidal breathing mode). In TIM mode, the adaptive aerosol delivery device guides patients to take a slow and deep breath through a feedback stimulus, and in the TBM mode, the patient guides the adaptive aerosol delivery device, which passively monitors the patient's breathing pattern to adapt an aerosol pulse duration. The medical aerosol delivery device comprises two different mouthpieces, one for each mode, and selects which mode to operate depending on the presence of which mouthpiece.

In other words, the adaptive aerosol delivery algorithm switches between the two modes when the adaptive aerosol delivery device e.g. detects the presence of a specific mouthpiece needed for the TIM mode. The TBM mode uses estimates of a tidal volume and an inhalation length averaged over three breaths to determine the duration of an aerosol pulse to use. The TIM mode sets a target inhalation time based on an inhalation length and adjusts the target inhalation time in small steps after each breath.

However, there are users who are confused over which mouthpiece to use. Another factor to be confused is that the two modes use vibration in different ways, the TBM mode as an indicator that the adaptive aerosol delivery device is working, the TIM mode as a target to aim for. Further, the users might have difficulties in adapting to the physical restriction in the TIM mouthpiece. Furthermore, having to provide two mouthpieces for the adaptive aerosol delivery device adds significant cost to the adaptive aerosol delivery device.

SUMMARY OF THE INVENTION

Hence, there may be a need to provide an improved control device for a medical aerosol delivery device, which is in particular easier to handle for the user.

The problem of the present invention is solved by the subject-matters of the independent claims, wherein further embodiments are incorporated in the dependent claims. It should be noted that the aspects of the invention described in the following apply also to the control device for a medical aerosol delivery device, the medical aerosol delivery system, the method for controlling a medical aerosol delivery device, the computer program element, and the computer readable medium.

According to the present invention, a control device for a medical aerosol delivery device is presented. The control device is configured to provide inhalation length data and to select an aerosol delivery mode from at least a first aerosol delivery mode or a different, second aerosol delivery mode based on the provided inhalation length data. The first aerosol delivery mode and the different, second aerosol delivery mode may be one of a target inhalation mode, a tidal breathing mode, a continuous aerosol delivery mode and breath-actuated delivery mode. In other words, the first aerosol delivery mode may be either a target inhalation mode, a tidal breathing mode, a continuous aerosol delivery mode, a breath-actuated delivery mode or the like, while the second aerosol delivery mode may be a different one of the target inhalation mode, the tidal breathing mode, the continuous aerosol delivery mode, the breath-actuated delivery mode or the like.

In an example, the control device comprises a provision unit and a control unit. The provision unit may be configured to provide the inhalation length data. The processing unit may be configured to select either a first aerosol delivery mode or a different, second aerosol delivery mode based on the provided inhalation length data.

The provided inhalation length data may be based on a user inhalation time detected during a user's previous inhalation. The provided inhalation length data may be provided inhalation length data per breath and may comprise or may be understood as one or several measured breathing signal (s), breathing value(s), inhalation duration(s), inhalation length(s) or inhalation time(s).

The first aerosol delivery mode may be a device guided mode, and preferably a target inhalation mode (TIM). The second aerosol delivery mode may be a user guided mode, and preferably a tidal breathing mode (TBM). TIM and TBM are further explained in the detailed description of the embodiments. The continuous aerosol delivery mode is a mode in which aerosol is continuously delivered. It may be useful if a tidal volume is extremely small to give a higher dose, for shorter treatment time for young paediatric patients and the like. The breath-actuated delivery mode is a mode in which aerosol is generated based on and during an entire inhalation.

The control device for a medical aerosol delivery device according to the invention may select the first or the second mode depending on the last inhalation time. Thereby, the control device for a medical aerosol delivery device allows for the use of only one mouthpiece for both modes and is, therefore, easier to handle for the user. In other words, the control device for a medical aerosol delivery device avoids using specific mouthpieces for each mode and the confusion and cost related to the former use of two different mouthpieces.

In an example, the control unit is further configured to calculate a target inhalation time for the user's subsequent inhalation based on the provided inhalation length data and the selection of the first or the second aerosol delivery mode.

In an example, in case the first aerosol delivery mode is selected, the control unit is configured to calculate the target inhalation time based on a target inhalation mode.

In an example, in case the second aerosol delivery mode is selected, the control unit is further configured to process the provided inhalation length data into a moving average value and preferably into a three-breath-moving average value and to calculate the target inhalation time based on this moving average value and preferably on this three-breath-moving average value. The moving average value can also be based on any other number of breaths, as e.g. a five-breath-moving average value, or weighted to remove the influence of older breaths, e.g. exponentially weighted moving average.

In an example, the control unit is further configured to calculate a target aerosol pulse length for the user's subsequent inhalation based on the target inhalation time and a breath hold value.

In an example, the control unit is further configured to control a switching of the aerosol delivery to a user between the first and the second aerosol delivery mode and to change between the two modes based on the provided inhalation length data. In an example, the switching may take between zero and ten seconds, preferably two seconds. In an example, the length of the switching is adjusted to force exclusively the first or the second aerosol delivery mode, e.g. setting the switch at zero forces exclusively the first mode and setting ten forces exclusively the second mode.

In an example, the control device comprises further comprises a feedback unit configured to indicate an end of the target inhalation time to the user by vibration, a visual and/or an audible signal.

According to the present invention, also a medical aerosol delivery system is presented. The medical aerosol delivery system comprises an aerosol delivery device and a control device as described above. The control device is configured to control the aerosol delivery device. The aerosol delivery device is configured to deliver aerosol to a user. The aerosol delivery device may be an adaptive aerosol delivery device for high end nebulizers such as Philips Ineb. The aerosol delivery device may be a mesh based nebulizer.

According to the present invention, also a method for controlling a medical aerosol delivery device is presented. The method comprises the following steps, not necessarily in this order:

a) providing inhalation length data, and
b) selecting either a first aerosol delivery mode or a different, second aerosol delivery mode based on the provided inhalation length data.

In an example, the method comprises a step to calculate a target inhalation time for the user's subsequent inhalation based on the provided inhalation length data and the selection of the first or the second aerosol delivery mode. In case the first aerosol delivery mode is selected, the method may comprise a step to calculate the target inhalation time based on a target inhalation mode. In case the second aerosol delivery mode is selected, the method may comprise a step to process the provided inhalation length data into a moving average value and preferably into a three-breath-moving average value and to calculate the target inhalation time based on this moving average value and preferably on this three-breath-moving average value. In an example, the method comprises a step to calculate a target aerosol pulse length for the user's subsequent inhalation based on the target inhalation time and a breath hold value.

According to the present invention, also a computer program element is presented, wherein the computer program element comprises program code means for causing the control device for a medical aerosol delivery device or the medical aerosol delivery system as defined in the independent device claims to carry out the steps of the method for controlling a medical aerosol delivery device as defined in the independent method claim when the computer program is run on a computer controlling the control device for a medical aerosol delivery device or the medical aerosol delivery system.

It shall be understood that the control device for a medical aerosol delivery device, the medical aerosol delivery system, the method for controlling a medical aerosol delivery device, the computer program element for controlling such device or system, and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings:

FIG. 1 shows a schematic drawing of an example of a medical aerosol delivery system with a control device.

FIG. 2 shows schematically and exemplarily how to choose between a device guided mode and a user guided mode.

FIG. 3 shows schematically and exemplarily how to calculate and adapt the device guided target inhalation time and pulse length.

FIG. 4 shows schematically and exemplarily how to calculate the user guided target inhalation time.

FIG. 5 shows basic steps of an example of a method for controlling a medical aerosol delivery device.

DETAILED DESCRIPTION OF EMBODIMENTS

FIG. 1 shows schematically and exemplarily an embodiment of a medical aerosol delivery system 1. The medical aerosol delivery system 1 comprises an aerosol delivery device 2 and a control device 10. The control device 10 controls the aerosol delivery device 2 and the aerosol delivery device 2 delivers aerosol to a user.

The control device provides inhalation length data and selects an aerosol delivery mode from at least a first aerosol delivery mode or a different, second aerosol delivery mode based on the provided inhalation length data. The first aerosol delivery mode and the different, second aerosol delivery mode are one of a target inhalation mode, a tidal breathing mode, a continuous aerosol delivery mode and breath-actuated delivery mode.

The control device 10 comprises a provision unit 11 and a control unit 13. The provision unit 11 provides inhalation length data. The provided inhalation length data is here based on a user inhalation time detected during a user's previous inhalation.

Figure 2:
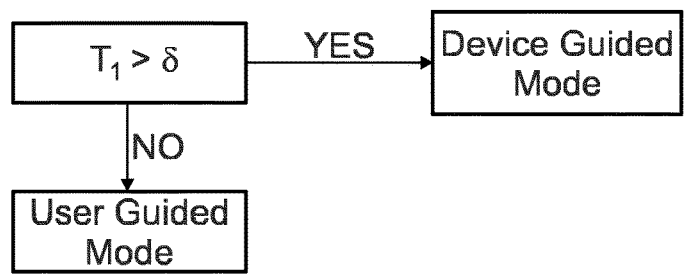

The processing unit selects either a first aerosol delivery mode or a different, second aerosol delivery mode based on the provided last inhalation length data, $T_I$, relative to a threshold, $\delta$, as shown schematically in FIG. 2. The first aerosol delivery mode is here a device guided mode, namely a target inhalation mode (TIM). The second aerosol delivery mode is here a user guided mode, namely a tidal breathing mode (TBM).

When the first or the second aerosol delivery mode is selected, the control unit 13 calculates a target inhalation time for the user's subsequent inhalation based on the provided inhalation length data and the selection of the first or the second aerosol delivery mode. In case the first aerosol delivery mode is selected, the control unit 13 calculates the target inhalation time based on a target inhalation mode. In case the second aerosol delivery mode is selected, the control unit 13 processes the provided inhalation length data into a three-breath-moving average value and calculates the target inhalation time based on this three-breath-moving average value. For both modes, a calculation of the target inhalation time will be shown in the following.

Figure 3:
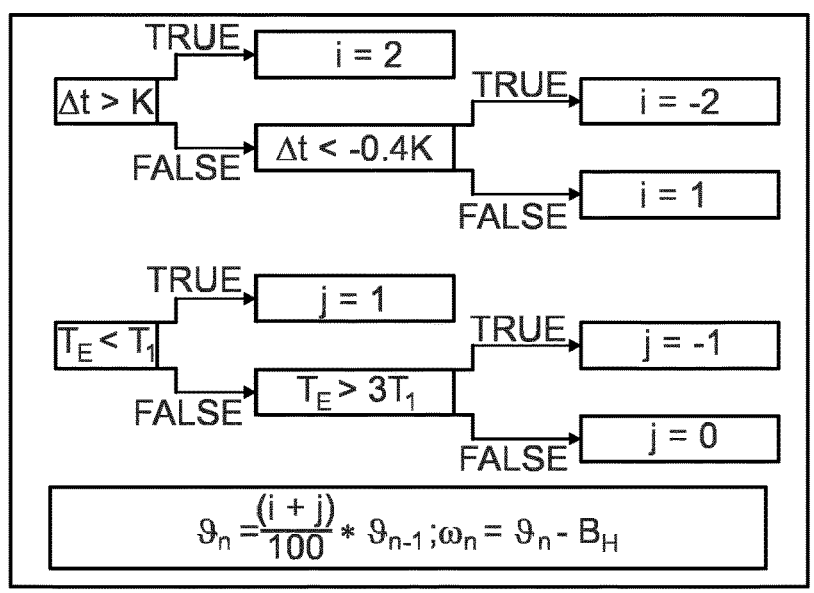

In case the first, the target inhalation (TIM) aerosol delivery mode is selected, the control unit 13 calculates the target inhalation time based on the target inhalation mode. FIG. 3 shows schematically and exemplarily how to calculate and adapt the target inhalation time. A duration between a signal to the user to exhale and an actual exhaling is $\Delta t$. A mere expected reaction time between the signal to the user to exhale and the actual exhaling is $\kappa$. The coefficients for determining the next target are i and j. If the duration $\Delta t$ is greater than a programmed threshold (e.g. 500 ms, to be programmable between 0 and 1000 ms), then the user may find the target inhalation volume too small and could be expected to cope with an increased target inhalation time. The target inhalation time is therefore increased by e.g. 2%. If the duration $\Delta t$ is less than a programmed threshold (e.g. −300 ms, to be programmable between 0 and 1000 ms), then the user has reacted very quickly to the feedback signal and may urgently need to exhale. This suggests that the user is unable to cope with such a long target inhalation time. The target inhalation time will be reduced by e.g. 2%.

Another factor is a duration of exhaling, $T_E$. If the duration of exhaling, $T_E$, is shorter than a last inhalation time, $T_I$, then the user may be desperate to reach the next inhalation. This would suggest that a minute volume dictated by the target inhalation time might be insufficient. The target inhalation time will therefore be increased by 1%. If the duration of exhaling, $T_E$, is long (greater than three times the inhalation duration, $3*T_I$), then this may indicate that the user has had to remove the medical aerosol delivery device 2 from his/her mouth and take multiple breaths to recover. The target inhalation time will therefore be reduced by 1%.

A maximum target inhalation time is determined using the inhalation time, exhalation time, reaction time and the previous maximum target inhalation time as shown above.

FIG. 3 further shows schematically and exemplarily how to calculate a target aerosol pulse length, $\omega_n$, for the user's subsequent inhalation as difference between the target inhalation time, $\theta_n$, and a breath hold value, $B_H$, for operation in device guided mode.

In case the second, the tidal breathing (TBM) aerosol delivery mode is selected, the control unit 13 processes the provided inhalation length data into a three-breath-moving average value and calculates the target inhalation time based on this three-breath-moving average value.

Figure 4:
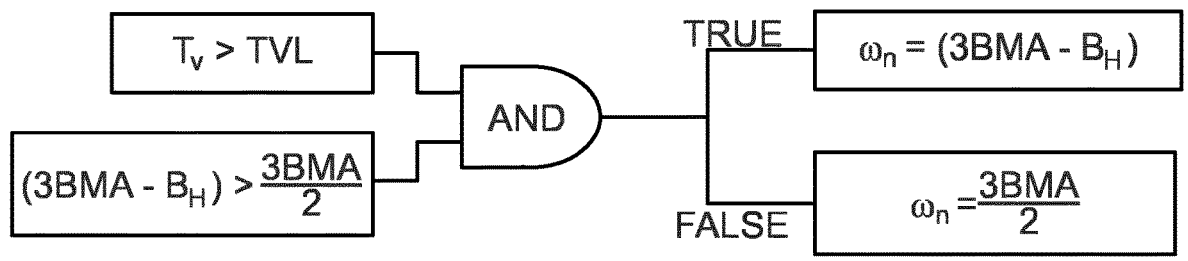

FIG. 4 shows schematically and exemplarily how to calculate a minimum target aerosol pulse length, $\omega_n$, for a user's subsequent inhalation based on an inhalation time, $T_I$, and a breath hold value, $B_H$, for operation in patient guided mode. If the calculated tidal volume, $T_V$, is less than a threshold TVL of e.g. 0.25 litres, or, a three breath moving average, 3BMA, minus the breath hold value, $B_H$, is less than half the three breath moving average, 3BMA, then the minimum target aerosol pulse length, $\omega_n$, is calculated as half of the three breath moving average. However, if the three breath moving average, 3BMA, minus the breath hold value, $B_H$, is greater than half three breath moving average, 3BMA, and the calculated tidal volume, $T_V$, is larger than the threshold TVL, then the aerosol pulse length, $\omega_n$, is the three breath moving average, 3BMA, minus the breath hold value, $B_H$.

If the inhalation time is greater than a threshold, $\delta$, of e.g. 2 seconds, then the target aerosol pulse length is a maximum target inhalation time minus the breath hold value and the target inhalation time is set to the maximum inhalation target time. Where the maximum target inhalation time is determined using the inhalation time, exhalation time, reaction time and the previous maximum target inhalation time as shown above. If the inhalation time is less than a threshold, $\delta$, of e.g. 2 seconds, then the target aerosol pulse is the minimum target aerosol pulse length and minimum target inhalation time is calculated as a percentage of a three-breath-moving average. This may be a value between 50 and 95%.

These determined values are stored in the medical aerosol delivery device 2 at the end of every inhalation cycle. When the medical aerosol delivery device 2 is switched on to begin a new treatment, the stored values are loaded and used. This means that the user can start the new treatment from the point at which the last finished.

FIG. 5 shows a schematic overview of steps of a method for controlling a medical aerosol delivery device 2. The method comprises the following steps, not necessarily in this order:

In a first step S1, providing inhalation length data.

In a second step S2, selecting either a first aerosol delivery mode or a different, second aerosol delivery mode based on the provided inhalation length data.

The method may comprise a further step to calculate a target inhalation time for the user's subsequent inhalation based on the provided inhalation length data and the selection of the first or the second aerosol delivery mode. In case the first aerosol delivery mode is selected, the method may comprise a step to calculate the target inhalation time based on a target inhalation mode. In case the second aerosol delivery mode is selected, the method may comprise a step to process the provided inhalation length data into a moving average value and preferably into a three-breath-moving average value and to calculate the target inhalation time based on this moving average value and preferably on this three-breath-moving average value. The method may comprise a further step to calculate a target aerosol pulse length for the user's subsequent inhalation based on the target inhalation time and a breath hold value.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A control device for a medical aerosol delivery device comprising:
    a provision unit, and
    a control unit,
    wherein the provision unit is configured to provide inhalation length data,
    wherein the control unit is configured to select an aerosol delivery mode from at least a first aerosol delivery mode or a different, second aerosol delivery mode based on the provided inhalation length data, wherein the first aerosol delivery mode is a target inhalation mode and the second aerosol delivery mode is a tidal breathing mode, and wherein in the target inhalation mode the control unit is configured to guide a user to breathe for a first target inhalation time and in the tidal breathing mode the control unit is configured to adapt a tidal breathing mode target aerosol pulse length and a second target inhalation time to the user's breathing pattern.

2. The control device according to claim 1, wherein the control unit is further configured to control a switching of the aerosol delivery between the first aerosol delivery mode and the second aerosol delivery mode and to change between the two modes based on the provided inhalation length data.

3. The control device according to claim 1, wherein the switching takes between zero and ten seconds.

4. The control device according to claim 1, wherein the provided inhalation length data is based on a user inhalation time detected during a user's previous inhalation.

5. The control device according to claim 1, wherein the control unit is configured to calculate the first target inhalation time or the second target inhalation time for the user's subsequent inhalation based on the provided inhalation length data and the selection of the first aerosol delivery mode or the second aerosol delivery mode.

6. The control device according to claim 5, further comprising a vibration unit configured to indicate an end of the target inhalation time to the user by vibration.

7. The control device according to claim 5, wherein, in case the first aerosol delivery mode is selected, the control unit is configured to calculate the first target inhalation time based on the target inhalation mode.

8. The control device according to claim 5, wherein, in case the second aerosol delivery mode is selected, the control unit is further configured to process the provided inhalation length data into a three-breath-moving average value and to calculate the second target inhalation time based on the three-breath-moving average value.

9. The control device according to claim 5, wherein the control unit is further configured to calculate a target inhalation mode target aerosol pulse length or the tidal breathing mode target aerosol pulse length for the user's subsequent inhalation based on a breath hold value and one of the first target inhalation time or the second target inhalation time.

10. A medical aerosol delivery system, comprising:
an aerosol delivery device, and
a control device comprising:
a provision unit, and
a control unit,
wherein the provision unit is configured to provide inhalation length data,
wherein the control unit is configured to select an aerosol delivery mode from at least a first aerosol delivery mode or a different, second aerosol delivery mode based on the provided inhalation length data, wherein the first aerosol delivery mode is a target inhalation mode and the second aerosol delivery mode is a tidal breathing mode, wherein in the target inhalation mode the control unit is configured to guide a user to breathe for a first target inhalation time and in the tidal breathing mode the control unit is configured to adapt a tidal breathing mode target aerosol pulse length and a second target inhalation time to the user's breathing pattern, and
wherein the aerosol delivery device is configured to deliver aerosol to a user.

11. The medical aerosol delivery system of claim 10, wherein the control unit is further configured to control a switching of the aerosol delivery between the first aerosol delivery mode and the second aerosol delivery mode and to change between the two modes based on the provided inhalation length data.

12. The medical aerosol delivery system of claim 11, wherein the switching takes between zero and ten seconds.

13. The medical aerosol delivery system of claim 10, wherein the provided inhalation length data is based on a user inhalation time detected during a user's previous inhalation.

14. The medical aerosol delivery system of claim 10, wherein the control unit is configured to calculate the first target inhalation time or the second target inhalation time for a user's subsequent inhalation based on the provided inhalation length data and the selection of the first aerosol delivery mode or the second aerosol delivery mode.

15. The medical aerosol delivery system of claim 14, further comprising a vibration unit configured to indicate an end of the first target inhalation time or the second target inhalation time to the user by vibration.

16. The medical aerosol delivery system of claim 14, wherein, in case the first aerosol delivery mode is selected, the control unit is configured to calculate the first target inhalation time based on the target inhalation mode.

17. The medical aerosol delivery system of claim 14, wherein, in case the second aerosol delivery mode is selected, the control unit is further configured to process the provided inhalation length data into a three-breath-moving average value and to calculate the second target inhalation time based on the three-breath-moving average value.

18. The medical aerosol delivery system of claim 14, wherein the control unit is further configured to calculate a target inhalation mode target aerosol pulse length or the tidal breathing mode target aerosol pulse length for the user's subsequent inhalation based on a breath hold value and one of the first target inhalation time or the second target inhalation time.

* * * * *